United States Patent [19]
Sancoff et al.

[11] Patent Number: 5,165,874
[45] Date of Patent: Nov. 24, 1992

[54] DISPOSABLE INFUSION APPARATUS AND PERISTALTIC PUMP FOR USE THEREWITH

[75] Inventors: Gregory E. Sancoff, Leucadia; Mark McWilliams, San Diego; Edward T. Cordner, Jr., Carlsbad, all of Calif.

[73] Assignee: Block Medical, Inc., Carlsbad, Calif.

[21] Appl. No.: 816,852

[22] Filed: Jan. 2, 1992

Related U.S. Application Data

[63] Continuation of Ser. No. 518,777, May 4, 1990, abandoned.

[51] Int. Cl.$^5$ ............................................. F04B 43/08
[52] U.S. Cl. .................................... 417/474; 417/360; 128/DIG. 12; 604/153
[58] Field of Search ............... 417/474, 475, 360; 128/DIG. 12; 604/153

[56] References Cited

U.S. PATENT DOCUMENTS

| | | | |
|---|---|---|---|
| 4,493,706 | 1/1985 | Borsanyi et al. | 417/474 |
| 4,565,542 | 1/1986 | Berg | 604/153 X |
| 4,653,987 | 3/1987 | Tsuji et al. | 417/474 X |
| 4,671,792 | 6/1987 | Borsanyi | 417/474 X |
| 4,798,590 | 1/1989 | O'Leary et al. | 417/477 X |
| 4,976,590 | 12/1990 | Baldwin | 417/477 X |
| 4,997,347 | 3/1991 | Roos | 417/475 |

Primary Examiner—Richard A. Bertsch
Assistant Examiner—Michael I. Kocharov
Attorney, Agent, or Firm—Baker, Maxham, Jester & Meador

[57] ABSTRACT

A disposable infusion apparatus includes proximal, distal and intermediate segments of IV tubing connected via couplings. The intermediate segment has a length sufficient for operative engagement with a pumping member of a peristaltic pump throughout a pumping stroke thereof. The intermediate segment further has a maximum Durometer of seventy-five on the Shore A scale. The pumping member includes a plurality of fingers mounted in side-by-side substantially parallel relationship for individual reciprocation. Motor driven cams individually reciprocate respective ones of the fingers in a predetermined timed sequence so that when the linearly disposed intermediate segment is squeezed by the fingers, intravenous fluid in the tubing will be pumped therethrough. The disposable apparatus further includes a door connected to opposite ends of the intermediate segment and which is releaseably loadable in a case to place the intermediate segment into operative engagement with the pumping member.

19 Claims, 3 Drawing Sheets

DISPOSABLE INFUSION APPARATUS AND PERISTALTIC PUMP FOR USE THEREWITH

This is a continuation of copending application Ser. No. 07/518,777 filed on May 4, 1990, now abandoned.

CROSS-REFERENCE TO RELATED APPLICATION

This application is related to co-pending U.S. patent application Ser. No. 07/518,987 entitled PROGRAMMABLE INFUSION SYSTEM filed on even date herewith, now U.S. Pat. No. 5,078,683.

BACKGROUND OF THE INVENTION

The present invention relates to medical devices, and more particularly, to an improved disposable infusion apparatus and peristaltic pump for delivering intravenous drugs at a controlled rate to a patient.

It is often necessary to intravenously supply patients with pharmaceutically active liquids over a long period of time at a controlled rate. It is desirable that this be accomplished while the patient is in an ambulatory state.

The prior art includes devices that employ a bag filled with fluid medication that feeds by gravity through IV tubing having drip or other controllers. It is difficult for a patient to be ambulatory with a gravity fed infusion device and flow control is very limited.

Another prior art infusion apparatus comprises an elastic bladder forming a liquid container mounted in an elongated cylindrical housing, a flow control valve, and tubing for supply of the liquid to the patient. The elastic walls of the bladder expand along the walls of the cylindrical housing when filled with the liquid, and provide the pressure for expelling the liquid. The bladder is typically filled by hand with a syringe which often requires an inordinate amount of force. Another drawback is that the bladder is forced to expand into an unnatural elongated configuration along the housing walls as it is filled. As a result of this unnatural configuration, the pressure of the bladder varies widely with the volume of liquid therein. Therefore, in most cases this type of elastic infusion apparatus does not have a reasonably stable pressure and flow rate over the infusion period. Most of such devices either have a flow rate that decreases with pressure, which decreases with volume, or one that remains roughly constant until the end where it surges. Attempts have been made to control pressure and flow rates by means of complicated and expensive flow control valves and devices. Other approaches have utilized exotic and expensive elastic materials in an effort to control the pressures and flow rates.

Another type of infusion apparatus employs a peristaltic or other positive displacement pump which is electrically driven. Programmable infusion pumps have been provided having the capability for precise tailoring of the fluid delivery rate parameters in four different modes, namely, continuous, intermittent, PCA (patient controlled analgesic) and TPN (total parenteral nutrition). Originally such programmable infusion pumps were large and not well suited for ambulatory patients. They used complex and expensive replacement pump cartridges to maintain sterility. More recently, small programmable infusion pumps have been available with disposable plastic cartridges that engage a peristaltic pump. However such cartridges have been bulky and expensive and have required excessive drive power in the pumps, leading to rapid battery drain.

Accordingly, it would be desirable to provide an improved disposable infusion apparatus and pump for delivering intravenous drugs at a controlled rate to an ambulatory patient.

SUMMARY OF THE INVENTION

It is therefore the primary object of the present invention to provide an improved disposable infusion apparatus and pump for delivering intravenous drugs at a controlled rate to an ambulatory patient.

In accordance with our invention a disposable infusion apparatus includes proximal, distal and intermediate segments of IV tubing connected via couplings. The intermediate segment has a length sufficient for operative engagement with a pumping member of a peristaltic pump throughout a pumping stroke thereof. The intermediate segment further has a maximum Durometer of seventy-five on the Shore A scale. The pumping member includes a plurality of fingers mounted in side-by-side substantially parallel relationship for individual reciprocation. Motor driven cams individually reciprocate respective ones of the fingers in a predetermined timed sequence so that when the linearly disposed intermediate segment is squeezed by the fingers, intravenous fluid in the tubing will be pumped therethrough. The disposable apparatus further includes a door connected to opposite ends of the intermediate segment and which is releaseably loadable in a case to place the intermediate segment into operative engagement with the pumping member.

DESCRIPTION OF THE PREFERRED EMBODIMENTS

Figure 1:
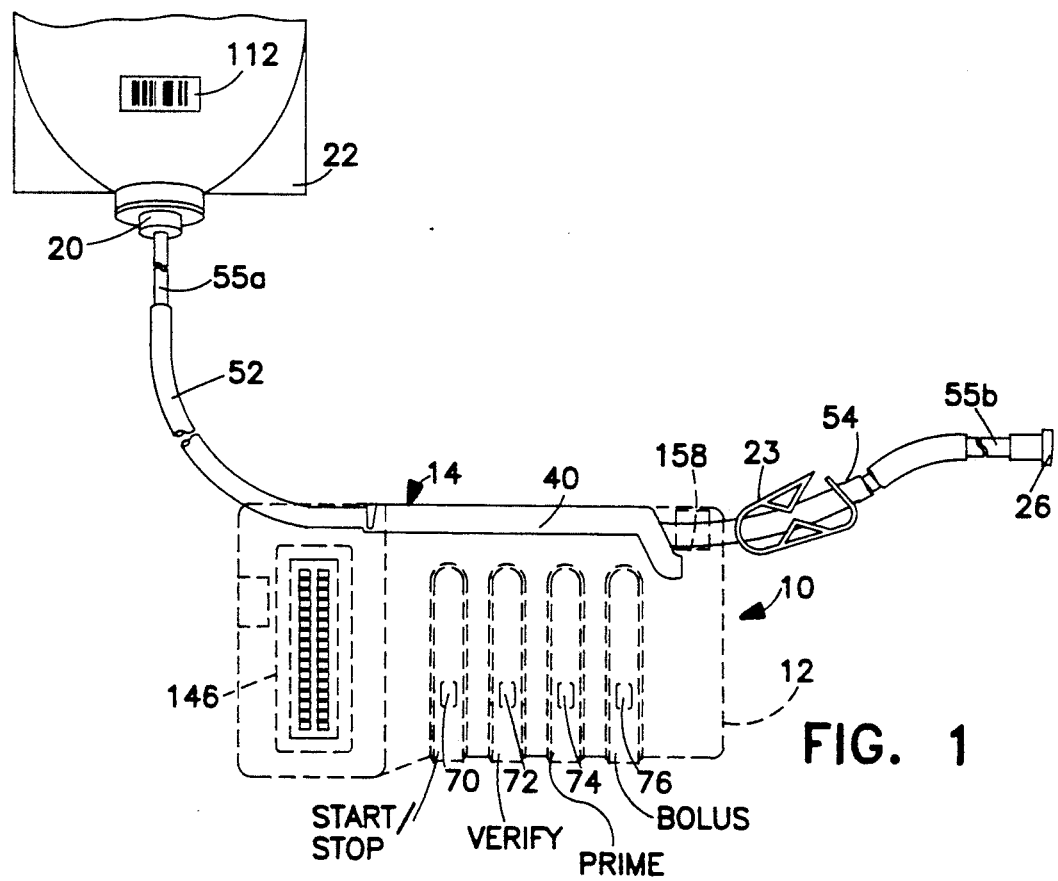
FIG. 1 illustrates a programmable infusion system in phantom lines with a preferred embodiment of our disposable apparatus loaded therein. The disposable is shown connected to conventional IV tubing segments, an IV bag, a spike connector and a leur fitting. The IV tubing segments are broken at various locations to make this figure more compact.

Referring to FIG. 1, a programmable infusion system 10 is illustrated which is adapted to utilize our disposable infusion apparatus and peristaltic pump. It includes a compact, portable rectangular case 12. By way of example, the case may be made of injection molded plastic and may measure approximately seven inches in length by approximately three and one-half inches in width (right side in FIG. 1) by approximately one inch in thickness (right side in FIG. 1).

The preferred embodiment of our disposable IV tubing apparatus 14 (FIG. 2) may be releasably loaded or installed in a receptacle protected position within an open 16 (FIG. 2) in a long side edge of the case 12. The proximal end disposable IV tubing apparatus 14 is connected to a conventional spike 20 (FIG. 1). The patient inserts the spike into a conventional bag 22 of intravenous fluid in which the desired medications are dissolved. The distal end of the disposable IV tubing apparatus 14 is connected to a conventional male leur fitting 26 which in turn connects to a conventional IV catheter (not illustrated). A disposable IV fluid conveying means is a necessary requirement in an infusion system since it ensures sterility. It also prevents residual amounts of medication from one IV drug administration from being inadvertently delivered when a new IV drug administration commences.

Figure 2:
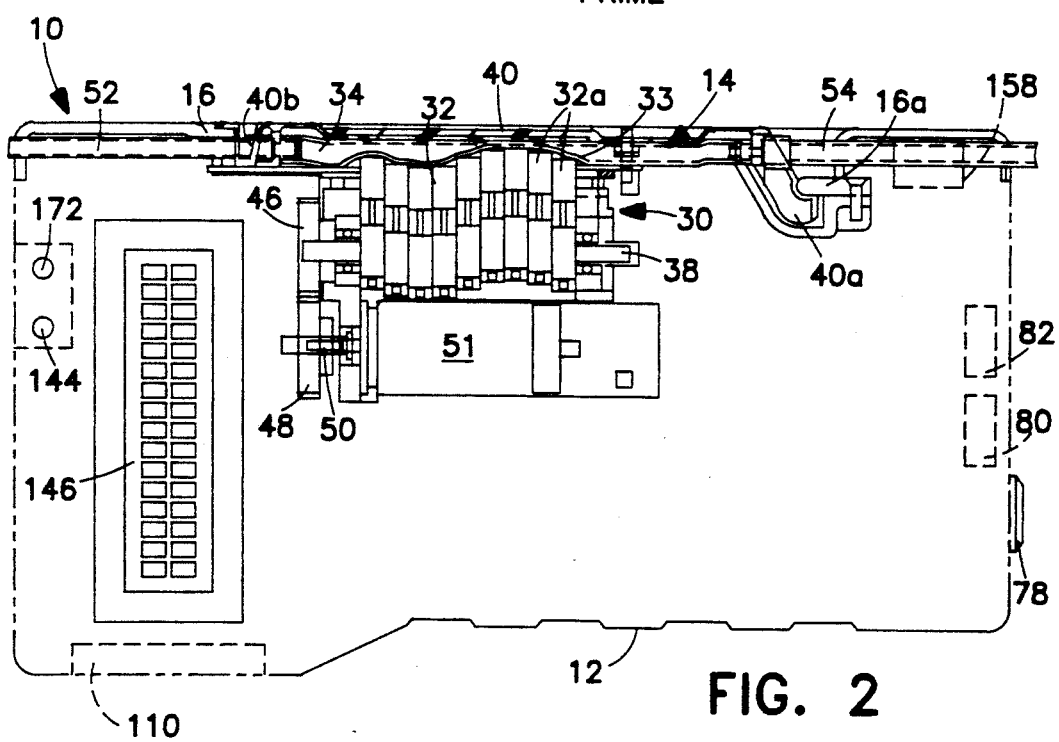
FIG. 2 is an enlarged fragmentary view of the programmable infusion system with the disposable apparatus installed therein and showing its relationship to a preferred embodiment of our peristaltic pump.
Figure 6:
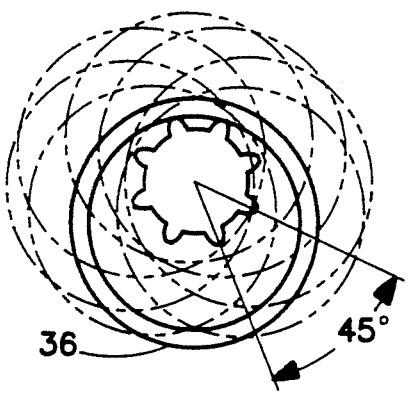
FIG. 6 is a side elevation view of one of the cam wheels of the perstaltic pump. The motion of the cam wheel is illustrated in phantom lines.

Referring to FIG. 2, the preferred embodiment of our peristaltic pump 30 is mounted inside the case 12 adjacent the receptacle 16. A pumping member 32 of the pump engages a linearly disposed intermediate segment 34 of the disposable IV tubing apparatus 14. The pumping member 32 comprises nine individual fingers 32a which slide back and forth toward and away from the intermediate IV tubing segment 34. The fingers 32a are moved by corresponding cam wheels 36 (FIG. 6). A flexible boot 33 (FIG. 2) surrounds the fingers and forms an interface between the fingers and the intermediate segment 34 of IV tubing. The peripheral edges of this boot are sealed to internal walls of the case to protect the pump from contamination. Each cam wheel 36 (FIG. 5) has a splined mounting hole 37 therethrough which is offset from the center of the wheel. Each finger 32a comprises a rectangular block having a circular hole in which a corresponding one of the cam wheels 36 rotates. The hole has a diameter slightly larger than the outside diameter of the wheel so that the wheel can rotate inside the hole and thereby pull the finger back and forth. The motion of one of the cam wheels is illustrated in phantom lines in FIG. 6.

The cam wheels 36 are mounted on a splined shaft 38 in progressive, offset alignment for individually reciprocating respective ones of the fingers 32a in a predetermined, timed sequence. The linearly disposed segment 34 of IV tubing is progressively squeezed by the fingers 32a so that intravenous fluid in the tubing is pumped therethrough.

Figure 5:
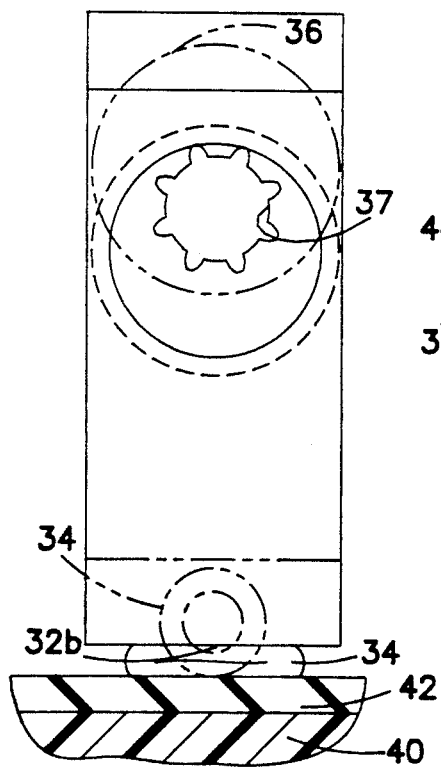
FIG. 5 is an enlarged side elevation view of one of the fingers of the perstaltic pump showing how it squeezes shut the intermediate tubing segment of the disposable.

The intermediate IV tubing segment 34 is preferably made of vinyl or silicone and has a maximum Durometer of seventy-five measured on the Shore A scale. By using a highly pliant, non-stiff resilient flexible tubing segment of this type, it is possible for the individual fingers 32a of the peristaltic pump 30 to each squeeze off and completely close the tubing segment during one cycle of its respective cam wheel. This squeezing off is illustrated in FIG. 5. This ensures a true positive displacement pump in which a single rotation of the splined shaft 38 will cause a predetermined volume of fluid to be pumped through the disposable IV tubing apparatus 14. Having such a non-stiff disposable IV tubing apparatus 14 also ensures that less torque is required to rotate the splined shaft 38, thereby resulting in an overall reduction in energy consumption when the peristaltic pump is electrically driven from battery power as hereafter described.

The fingers 32a preferably have small teats 32b (FIG. 5) projecting from the ends thereof. These teats engage and squeeze the intermediate IV tubing segment 34. It has been determined that these teats ensure that the tubing segment 34 will be completely squeezed off during each cycle of each finger. It is important to understand that the intermediate tubing segment 34 must have a minimum amount of stiffness and resilience or else it will not open and close in a manner that will permit it to function as a peristaltic pump. Preferably the tubing segment 34 has a minimum Durometer of thirty-five measured on the Shore A scale.

Referring again to FIG. 2, the programmable infusion system 10 includes means for releasably mounting the intermediate IV tubing segment 34 adjacent the pumping member 32. The intermediate tubing segment 34 is mounted to a door 40 having a hook-shaped member 40a (FIG. 3) at one end and a compressible clasp 40b at the other end. The hook-shaped member 40a of the door may be engaged by the patient with a shoulder 16a (FIG. 2) located at one end of the receptacle 16 in the case 12. The other end of the door is then swung in and the clasp 40b snaps into the other end of the receptacle 16. The intermediate IV tubing segment 34 is squeezed between the individual fingers 32a and a compressible, resilient pad 42 (FIGS. 3 and 5) supported by the innerside of the door 40. This pad may be made of polyurethane foam.

The shaft 38 (FIG. 3) which supports the cam wheels 36 is journaled at opposite ends in ball bearings 44. A gear 46 rigidly mounted on one end of the shaft 38 meshes with another gear 48 (FIG. 2) rigidly mounted on another shaft 50 of a DC motor module 51 having an internal 141:1 gear reduction. In other words, one-hundred and forty-one rotations of the armature of the DC motor turns the shaft 50 one revolution and thus the cam shaft 38 one revolution.

Figure 4:
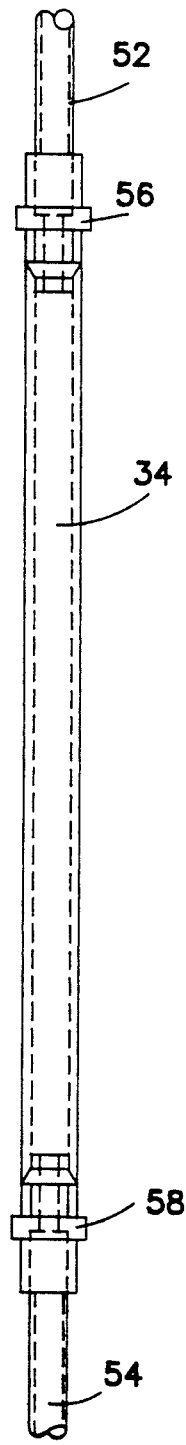
FIG. 4 is an enlarged view of the three segments of tubing that form part of the disposable.

Referring to FIG. 4, the disposable IV tubing apparatus 14 has a proximal tubing segment 52 and a distal tubing segment 54 connected to opposite ends of the intermediate IV tubing segment 34 by means of couplings 56 and 58. These couplings are attached to the underside of the door 40 as hereafter described in conjunction with FIG. 9.

Referring to FIG. 4, the intermediate IV tubing segment 34 preferably has an inside diameter of approximately 0.125 inches. Silicone and VINYL tubing can be commercially obtained having the desired stiffness. The proximal segment 52 and the distal segment 54 are each preferably made of clear polyvinyl chloride (PVC) having an outside diameter of approximately 0.140 inches and an inside diameter of approximately 0.088 inches. This clear PVC tubing is larger in both inside and outside diameter than the conventional PVC tubing segments 55a and 55b (FIG. 1) which connect the segments 52 and 54 to the spike 20 and male lure fitting 26, respectively.

In an actual prototype of our preferred embodiment, the designed maximum delivery rate is approximately three hundred milliliters per hour. The minimum designed delivery rate is approximately 0.1 milliliters per hour. The delivery resolution is approximately 0.1 milliliters per hour for 0.01 through 99.9 milliliters per hour and approximately one milliliter per hour for approximately one hundred to three hundred milliliters per hour. In the prototype, the designed maximum volume to be infused (VTBI) is one thousand milliliters and the minimum volume to be infused (VTBI) is approximately 0.1 milliliters. The designed "keep vein open" (KVO) rate is approximately one milliliter per hour for one through three hundred milliliter per hour rates and approximately 0.1 through 0.99 milliliters per hour for 0.1 through 0.99 milliliter per hour rates.

Figure 7:
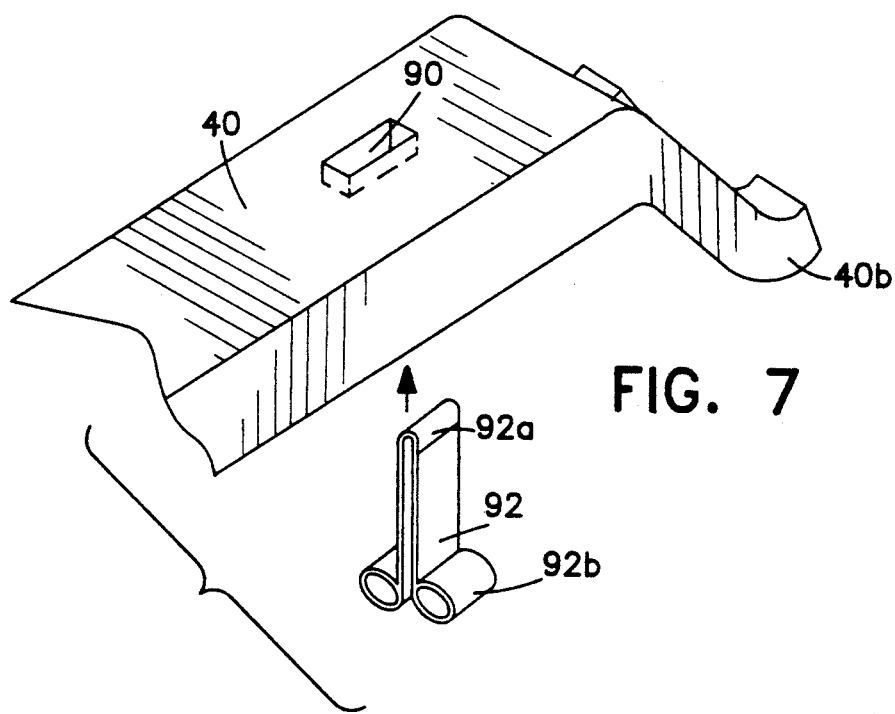
FIGS. 7–9 illustrate details of the disposable door, tube clamp and IV tubing couplings.
Figure 8:
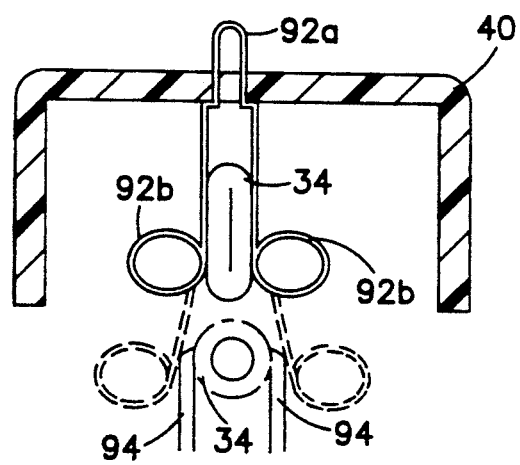

Referring to FIG. 7, the door 40 has a rectangular aperture 90 formed adjacent the hook-shaped member 40a. A resilient metal tubing squeezer 92 has an upper end 92a which is tightly received in the aperture 90 in the door 40. The squeezer 92 has a pair of parallel downwardly extending arms which terminate in coiled sections 92b. Referring to FIG. 8, when the disposable is assembled, the intermediate segment 34 is squeezed shut between the coiled sections 92b. When the door 40 is installed into the receptacle 16 of the case 12, the hook-shaped member 40a is engaged with the shoulder 16a (FIG. 2). The other end of the door having the clasp 40b is then swung toward the case. As this happens, the coiled sections 92b of the tubing squeezer 92 engage upstanding projections 94 (FIG. 8) in the receptacle. These projections are spaced so that the coiled sections are displaced outwardly away from the intermediate tubing segment 34 thereby unclamping the same. This is illustrated in phantom lines in FIG. 8. The squeezer performs a very important function. Namely, if the disposable IV tubing apparatus 14 should be inadvertently removed from the case 12 it will squeeze off the intermediate tubing section 34 and prevent freeflow of intravenous fluid by gravity action.

Figure 3:
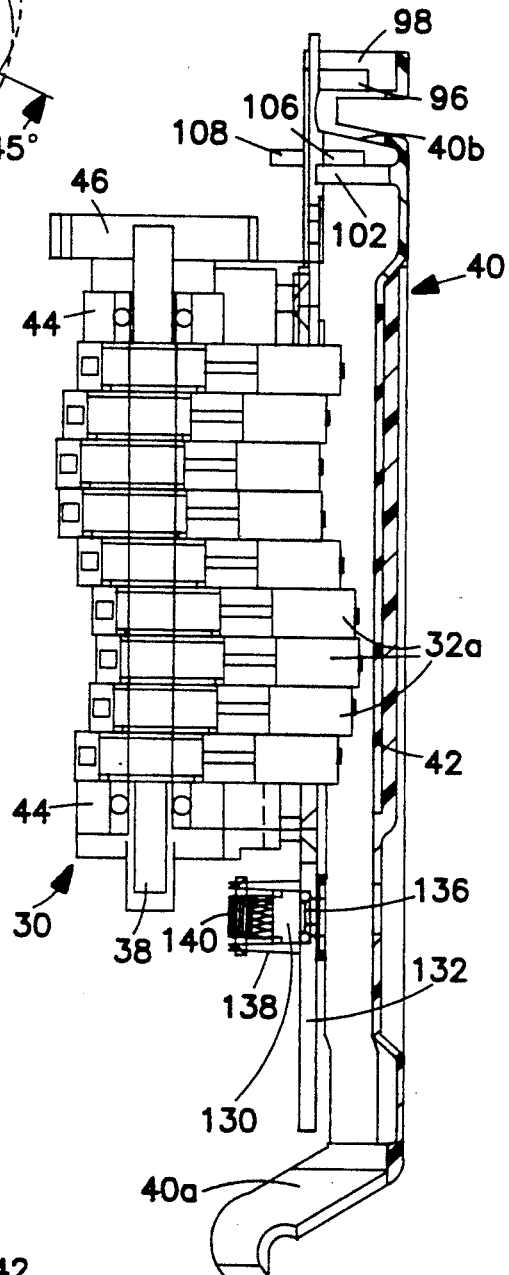
FIG. 3 is a further enlarged view of the perstaltic pump and the door of the disposable. The IV tubing segments are not shown in this figure.

Referring to FIG. 3, the clasp 40b consists of a V-shaped element. The door 40 is preferably made of injection molded plastic and the V-shaped clasp 40b is compressible upon swinging the clasp into the receptacle 16 in the case. This allows a wedge-shaped projection 96 on the clasp 40b to clear and snap into engagement behind an L-shaped latch 98.

Figure 9:
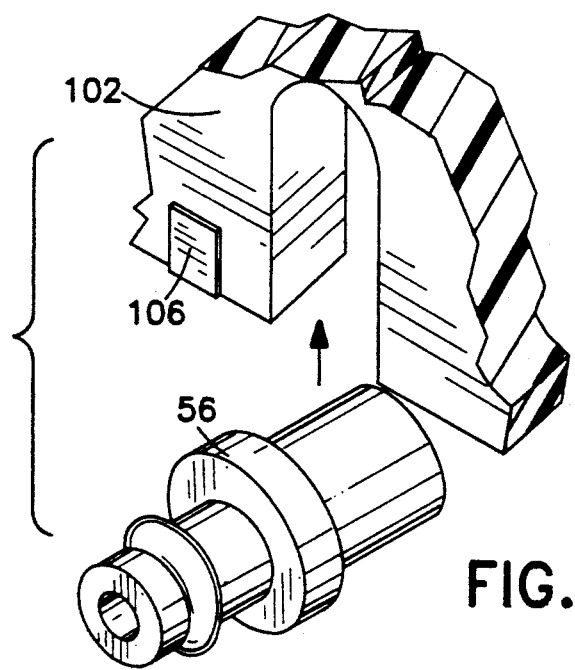

Further details of the disposable IV tubing apparatus 14 are visible in FIG. 9. The coupling 56 is received in a slot in a bracket 102 which extends from the underside of the exterior wall of the door 40 near the clasp 40b. The coupling 56 is solvent, welded or bonded to the bracket 102. The coupling 58 is similarly received in another recess formed in the hook-shaped member 40a. Again the coupling 58 is solvent bonded to the member 40a. A magnet 106 (FIG. 9) is attached to the bracket 102 and detected by a Hall effect switch 108 (FIG. 3) adjacent the receptacle 16. The Hall effect switch is connected to the micro-controller hereafter described so that the output thereof will indicate whether or not a disposable has been correctly loaded into the case 12. The peristaltic pump 30 is a single channel, linear peristaltic pump having nine reciprocating fingers 32a. The intermediate IV tubing segment 34 is highly flexible as previously indicated. In a preferred embodiment of the disposable 14, the intermediate IV tubing segment 34 is made of silicone and has an inside diameter of approximately 0.125 inches. Approximately 0.12 milliliters of intravenous fluid are pumped through the intermediate IV tubing segment 34 for each single revolution of pump shaft 38. The combined motor and gear reduction module 51 also preferably includes a built-in motor encoder. One suitable unit is the MICRO-MO Model 1624006S. It uses TEFLON (Trademark) fixotropic lubricant. A conventional Robert's clamp 23 (FIG. 1) may be provided on the segment of conventional IV tubing 55b for closing off the same.

While we have described preferred embodiments of our improved disposable infusion apparatus and peristaltic pump for use therewith, it should be understood that modifications and adaptations thereof will occur to persons skilled in the art. Therefore, the protection afforded our invention should only be limited in accordance with the scope of the following claims.

We claim:

1. An infusion apparatus comprising in combination:
    a portable hand held peristaltic pump mounted in a case, the case having an open receptacle within the case and an opening extending from the receptacle into the case, and the pump having a plurality of reciprocable pumping fingers disposed adjacent and extending to said opening in said case;
    a unitary door and support member for direct support of an intermediate segment of IV tubing and having detachable hook shaped hinge means on one end thereof for engaging shoulder means in one end of said receptacle and releasable V-shaped latch means on the other end thereof for engaging shoulder means in the other end of said receptacle, said unitary door and support member being detachably mounted in a substantially fully recessed positioned within said receptacle and covering said opening;
    an intermediate segment of IV tubing having a maximum Durometer of seventy-five on the Shore A scale mounted directly on said door for positioning over said opening for operative engagement with said pumping fingers of the peristaltic pump, the intermediate segment having a length sufficient for operative engagement with said pumping fingers of the peristaltic pump throughout a pumping stroke thereof;
    a proximal segment of IV tubing connected to a first end of the intermediate segment of IV tubing; and
    a distal segment of IV tubing connected to a second end of the intermediate segment of IV tubing.

2. A disposable infusion apparatus according to claim 1 wherein the intermediate segment of IV tubing is made of a material selected from the group consisting of VINYL and silicone.

3. A disposable infusion apparatus according to claim 1 wherein the intermediate segment of IV tubing has a minimum Durometer of thirty-five on the Shore A scale.

4. A disposable infusion apparatus according to claim 1 wherein the proximal segment of IV tubing is made of polyvinyl chloride.

5. A disposable infusion apparatus according to claim 1 wherein the distal segment of IV tubing is made of polyvinyl chloride.

6. A disposable infusion apparatus according to claim 1 wherein the hinge means includes a hook-shaped member.

7. A disposable infusion apparatus according to claim 1 wherein said peristaltic pump comprises:
    means for mounting said plurality of fingers in side-by-side substantially parallel relationship for individual reciprocation;
    cam means for individually reciprocating respective ones of the fingers in a predetermined time sequences so that when a linearly disposed segment of IV tubing is squeezed by the fingers intravenous fluid in the tubing will be pumped therethrough; and
    motor means for driving the cam means.

8. A disposable infusion apparatus according to claim 7 further comprising a flexible boot surrounding the fingers and forming an interface between the fingers and the segment of IV tubing.

9. A disposable infusion apparatus according to claim 8 wherein each finger has a ridge projecting therefrom for engaging the segment of IV tubing and ensuring the complete squeezing off thereof.

10. A disposable infusion apparatus according to claim 9 wherein the cam means includes a splined shaft and a plurality of identical cam wheels, each cam wheel having a splined mounting hole therethrough offset from a center of the wheel, and the wheels being mounted on the splined shaft in progressive offset alignment for individually engaging and reciprocating respective ones of the fingers in the predetermined timed sequence.

11. A disposable infusion apparatus comprising in combination:
a portable hand held peristaltic pump mounted in a portable case, the case having an elongated open receptacle in one side thereof and an opening extending from the receptacle into the case, and the pump having a plurality of reciprocable pumping fingers disposed in said case adjacent and extendable through said opening in said case into said elongated receptacle;
an elongated unitary door and support member for direct support of an intermediate segment of IV tubing and being detachably mounted in a substantially fully recessed position within said receptacle and having a planar backing wall covered by a compressible resilient pad for positioning over said opening, a hook-shaped hinge member on one end of said door for engaging a shoulder in one end of said receptacle, a V-shaped releasable latch clasp on the other end of said door for releasably engaging a latching shoulder in the other end of said receptacle;
an intermediate segment of IV tubing having a minimum Durometer of thirty-five and a maximum Durometer of seventy-five on the Shore A scale mounted on said door over said planar backing surface for positioning over said opening when said elongated unitary door and support member is mounted within said receptacle, and having a length sufficient for operative engagement with the pumping fingers of the peristaltic pump throughout a pumping stroke thereof and being squeezed between said resilient pad on said backing surface and said pumping fingers;
an elongated proximal segment of IV tubing;
means for connecting an end of the proximal segment of IV tubing to a first end of the intermediate segment of IV tubing;
an elongated distal segment of IV tubing; and
means for connecting an end of the proximal segment of IV tubing to a second end of the intermediate segment of IV tubing.

12. A disposable infusion apparatus according to claim 11 wherein the intermediate segment of IV tubing is made of a material selected from the group consisting of VINYL and silicone.

13. A disposable infusion apparatus according to claim 12 wherein the proximal segment and the distal segment of IV tubing is made of polyvinyl chloride.

14. A disposable infusion apparatus according to claim 11 wherein the intermediate segment of IV tubing is made of silicone rubber.

15. A disposable infusion apparatus for use with a peristaltic pump, comprising:
a proximal segment of IV tubing;
a distal segment of IV tubing;
an intermediate segment of IV tubing having a maximum Durometer of seventy-five on the Shore A scale, the intermediate segment having a length sufficient for operative engagement with a pumping member of a peristaltic pump throughout a pumping stroke thereof;
a first coupling connecting a first end of the proximal segment of IV tubing to a first end of the intermediate segment of IV tubing;
a second coupling connecting a first end of the distal segment of IV tubing to a second end of the intermediate segment of IV tubing;
means for releasably mounting the intermediate segment adjacent the pumping member comprising a door secured to the first and second ends of the intermediate segment of IV tubing, and releasably engageable with a portion of a case defining a receptacle for positioning the intermediate segment of IV tubing in engagement with the pumping member of the peristaltic pump when it is mounted in the case adjacent the receptacle;
hinge means on a first end of said door for engaging the portion of the case defining the receptacle at a first end thereof for permitting a second end of the door means to swing toward and away from the case; and
tube squeezer means connected to the door for normally squeezing the intermediate segment of IV tubing shut and actuable upon engagement with the case to open the intermediate segment of IV tubing.

16. A disposable infusion apparatus according to claim 15 wherein said peristaltic pump comprises:
means for mounting said plurality of fingers in side-by-side substantially parallel relationship for individual reciprocation;
cam means for individually reciprocating respective ones of the fingers in a predetermined timed sequence so that when a linearly disposed segment of IV tubing is squeezed by the finger, intravenous fluid in the tubing will be pumped therethrough; and
motor means for driving the cam means.

17. A disposable infusion apparatus according to claim 16 further comprising a flexible boot surrounding the fingers and forming an interface between the fingers and the segment of IV tubing.

18. A disposable infusion apparatus according to claim 17 wherein each finger has a ridge projecting therefrom for engaging the segment of IV tubing and ensuring the complete squeezing off thereof.

19. A disposable infusion apparatus according to claim 18 wherein the cam means includes a splined shaft and a plurality of identical cam wheels, each cam wheel having a splined mounting hole therethrough offset from a center of the wheel, and the wheels being mounted on the splined shaft in progressive offset alignment for individually engaging and reciprocating respective ones of the fingers in the predetermined timed sequence.

* * * * *